(12) United States Patent
Krishnan et al.

(10) Patent No.: US 10,971,255 B2
(45) Date of Patent: Apr. 6, 2021

(54) MULTIMODAL LEARNING FRAMEWORK FOR ANALYSIS OF CLINICAL TRIALS

(71) Applicant: Zasti Inc., Oakton, VA (US)

(72) Inventors: Ramanathan Krishnan, Oakton, VA (US); John Domenech, Big Pine Key, FL (US); Rajagopal Jagannathan, Chennai (IN); Sharath Makki Shankaranarayana, Chennai (IN)

(73) Assignee: ZASTI INC., Oakton, VA (US)

( * ) Notice: Subject to any disclaimer, the term of this patent is extended or adjusted under 35 U.S.C. 154(b) by 0 days.

(21) Appl. No.: 16/570,942

(22) Filed: Sep. 13, 2019

(65) Prior Publication Data

US 2020/0090796 A1 Mar. 19, 2020

Related U.S. Application Data

(60) Provisional application No. 62/731,793, filed on Sep. 14, 2018.

(51) Int. Cl.
| | | |
|---|---|---|
| *G16H 10/60* | (2018.01) | |
| *G16H 15/00* | (2018.01) | |
| *G06N 20/00* | (2019.01) | |
| *G16H 10/20* | (2018.01) | |

(52) U.S. Cl.
CPC ............ *G16H 10/60* (2018.01); *G06N 20/00* (2019.01); *G16H 10/20* (2018.01); *G16H 15/00* (2018.01)

(58) Field of Classification Search
CPC ....... G06T 7/0012; G16H 50/20; G16H 10/60
See application file for complete search history.

(56) References Cited

U.S. PATENT DOCUMENTS

| | | | |
|---|---|---|---|
| 9,536,194 B2 | 1/2017 | Cao et al. | |
| 9,754,220 B1 | 9/2017 | Brestoff et al. | |
| 10,327,709 B2 | 6/2019 | Heldt et al. | |
| 2004/0101181 A1* | 5/2004 | Giger | G06T 7/0012 |
| | | | 382/128 |
| 2007/0105136 A1 | 5/2007 | Staudt et al. | |
| 2007/0248948 A1 | 10/2007 | Hatzis et al. | |
| 2008/0033894 A1 | 2/2008 | Steck et al. | |
| 2009/0234627 A1 | 9/2009 | Yu et al. | |
| 2010/0057651 A1 | 3/2010 | Fung et al. | |
| 2012/0269418 A1* | 10/2012 | McCulloch | G01N 33/57434 |
| | | | 382/133 |
| 2013/0116511 A1* | 5/2013 | Sui | G16B 40/00 |
| | | | 600/300 |
| 2013/0262357 A1 | 10/2013 | Amarasingham et al. | |

(Continued)

FOREIGN PATENT DOCUMENTS

| | | |
|---|---|---|
| CN | 107133481 A | 9/2017 |
| WO | 2014/137892 A1 | 9/2014 |

OTHER PUBLICATIONS

Hothorn et al., "Survival ensembles," Biostatistics, pp. 355-373, Dec. 12, 2005.

(Continued)

*Primary Examiner* — Reginald R Reyes
(74) *Attorney, Agent, or Firm* — Seed IP Law Group LLP

(57) ABSTRACT

A facility providing a medical outcome prediction model data structure is described. The data structure constitutes a trained statistical model that can be applied to image data and electronic health record data for a patient to predict a cancer survival outcome for the patient.

18 Claims, 11 Drawing Sheets

(56) References Cited

U.S. PATENT DOCUMENTS

| | | |
|---|---|---|
| 2014/0279754 A1 | 9/2014 | Barsoum et al. |
| 2016/0140442 A1 | 5/2016 | Lee et al. |
| 2016/0283679 A1 | 9/2016 | Hu et al. |
| 2017/0323063 A1 | 11/2017 | Krause et al. |
| 2017/0357760 A1 | 12/2017 | Han et al. |
| 2018/0018757 A1 | 1/2018 | Suzuki |
| 2018/0107791 A1 | 4/2018 | Guo et al. |
| 2018/0158552 A1 | 6/2018 | Liu et al. |
| 2018/0348235 A1* | 12/2018 | Vigue .................... G01N 33/74 |
| 2019/0378619 A1 | 12/2019 | Meyer et al. |

OTHER PUBLICATIONS

Watt, "Exploring Temporal Frameworks for Constructing Longitudinal Instance-Specific Models from Clinical Data," 2012, UMI, ProQuest, 252 pages.

Zhang, "Mining Clinical Data for Trauma Patients," Sep. 2016, ProQuest, 125 pages.

* cited by examiner

FIG. 10

MULTIMODAL LEARNING FRAMEWORK FOR ANALYSIS OF CLINICAL TRIALS

CROSS-REFERENCE TO RELATED APPLICATION(S)

This application claims the benefit of U.S. Provisional Patent Application No. 62/731,793, filed on Sep. 14, 2018, which is hereby incorporated by reference in its entirety. Where a document incorporated herein by reference conflicts with the present application, the present application controls.

BACKGROUND

Clinical trials are of great importance to study the effectiveness of new treatment regimens. During clinical trials, different groups of patients are subject to different types of drugs and the patients are made to undertake several clinical tests and are usually followed up multiple times. Events such as death, progression of disease, development of adverse reaction, etc., are of particular importance.

BRIEF DESCRIPTION OF THE DRAWINGS

FIGS. 9-11 are display diagrams showing a sample patient test results report presented by the facility in some embodiments.

DETAILED DESCRIPTION

Figure 1:
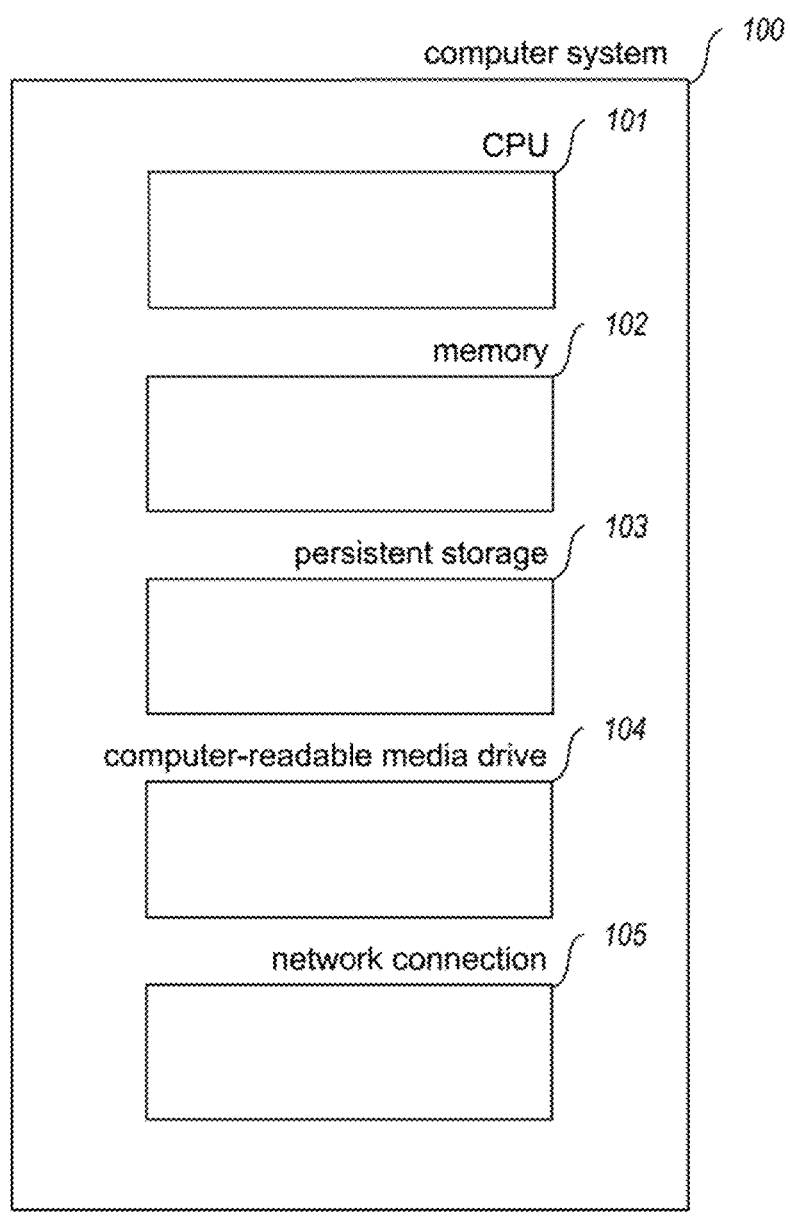
FIG. 1 is a block diagram showing some of the components typically incorporated in at least some of the computer systems and other devices on which the facility operates.

The inventors have recognized that analysis of clinical trials is of paramount importance to many clinicians and trialists, since it helps them to study disease progression in patients and monitor the effectiveness of a drug for a particular disease. To this end, they have conceived and reduced to practice a software and/or hardware facility that provides a multimodal learning based framework for predicting key outcomes in clinical trials ("the facility"). The facility extracts the clinical data and/or other information from multiple modalities like electronic health records (EHR), including text and numerical data and also image data which in the field of healthcare is often in the form of computed tomography (CT) scans, radiological images of other types, or annotation markings. The facility helps in the quantitative assessment of the disease under consideration, such as various forms of cancer.

In some embodiments, the facility provides a multimodal learning-based framework for prediction of key outcomes in clinical trials such as overall survival of a patient, disease-free progression survival of a patient, probability of adverse events, etc.

In some embodiments, the facility performs data-driven patient grouping across trials into multiple categories, analysis of similarities in presentation and response, and suggestions for informative parameters. This helps the clinicians by providing informative cues, and also serves as a tool for trialists to perform patient matching.

In some embodiments, the facility provides a dashboard for caregivers for the continuous monitoring of early response, anticipatory treatment based on predicted adverse reactions and predicted response, planning treatment durations.

In various embodiments, the facility can employ any clinical trial data of multiple modalities such as image, text, etc., and extract features, and produce informative report on the clinical trial.

Cancer can be viewed as a heterogeneous disease with many different subtypes. Cancer patients undergoing different kinds of treatments can be subjected to various clinical tests at multiple intervals, and also subjected to different imaging tests such as computed tomography (CT) or magnetic resonance imaging (MRI) scans. Since cancer cases worldwide are on a rise, early diagnosis and prognosis of cancer is of increasing benefit. The facility also help in the subsequent clinical management of patients. Studying and modeling the prognosis of cancer and thereby identifying the risk indices of cancer patients is an area of active research and of significant interest.

Three predictive tasks of interest are: (i) the prediction of cancer susceptibility (risk assessment), (ii) the prediction of cancer recurrence/local control and (iii) the prediction of cancer survival. In the first two cases, one is trying to find (i) the likelihood of developing a type of cancer and (ii) the likelihood of redeveloping a type of cancer after complete or partial remission. In the last case, the prediction of a survival outcome such as disease-specific or overall survival after cancer diagnosis or treatment is the main objective. The prediction of cancer outcome often refers to assessment of (a) life expectancy, (b) survivability, (c) progression, and/or (d) treatment sensitivity.

In some embodiments, the facility is integrated with electronic health record logging system. The electronic health record consists of an individual patient's information, and the record is constantly updated by the clinicians or trialists. The facility directly predicts the key outputs such as overall survival of the patient and progression free survival of the patient and other informative predictions of interests to the clinicians or trialists. The predictions can be performed on a standalone computer or a cloud computing architecture.

In some embodiments, the facility operates as a teleconsulting service in which the learning framework need not reside at the site of trial or clinic which logs in the patient electronic health record data, but the electronic health record data transmitted over internet to a remote computer hosting our learning framework in the prediction mode. The report is prepared remotely and can be proof-read at a third remote location. The final report can be relayed back to the clinicians or trialists.

The facility can also be used for other kinds of survival analysis tasks which also contains information in the form of images along with textual data.

By performing in some or all of these ways, the facility provides insights into clinical trials, and uses the data they produce to predict treatment efficacy in other patients.

FIG. 1 is a block diagram showing some of the components typically incorporated in at least some of the computer systems and other devices on which the facility operates. In various embodiments, these computer systems and other devices 100 can include server computer systems, cloud computing platforms or virtual machines in other configurations, desktop computer systems, laptop computer systems, netbooks, mobile phones, personal digital assistants, televisions, cameras, automobile computers, electronic media players, etc. In various embodiments, the computer systems and devices include zero or more of each of the following: a central processing unit ("CPU") 101 for executing computer programs; a computer memory 102 for storing programs and data while they are being used, including the facility and associated data, an operating system including a kernel, and device drivers; a persistent storage device 103, such as a hard drive or flash drive for persistently storing programs and data; a computer-readable media drive 104, such as a floppy, CD-ROM, or DVD drive, for reading programs and data stored on a computer-readable medium; and a network connection 105 for connecting the computer system to other computer systems to send and/or receive data, such as via the Internet or another network and its networking hardware, such as switches, routers, repeaters, electrical cables and optical fibers, light emitters and receivers, radio transmitters and receivers, and the like. While computer systems configured as described above are typically used to support the operation of the facility, those skilled in the art will appreciate that the facility may be implemented using devices of various types and configurations, and having various components.

Healthcare data includes data in the form of clinical tests, electronic health records (EHR) or text. It also contains significant data in the form of images as computed tomography (CT) scans or magnetic resonance imaging (MRI) scans, etc. Most work in learning-based cancer survival prediction utilize only clinical variables. The facility utilizes both clinical data as well as imaging data.

Figure 2:
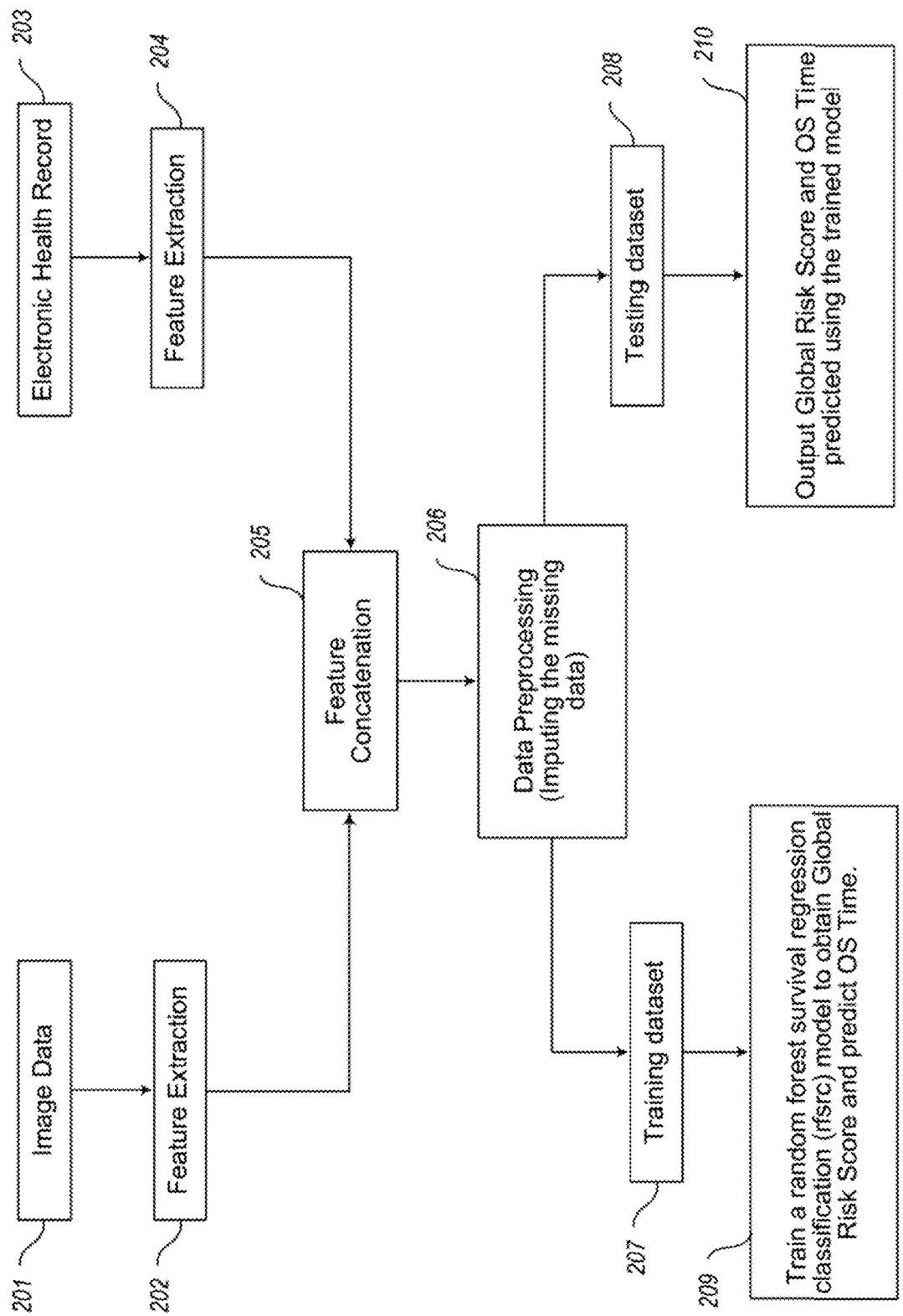
FIG. 2 is a flow diagram showing a process performed by the facility in some embodiments to train and apply a model for predicting medical outcomes for patients, such as global risk score and overall survival time.

FIG. 2 is a flow diagram showing a process performed by the facility in some embodiments to train and apply a model for predicting medical outcomes for patients, such as global risk score and overall survival time. In act 201, the facility accesses patient image data, such as CT or MRI scans. In act 202, the facility processes the image data to extract image-based features.

In the case of cancer analysis, some useful image features are average intensity in the tumor region, volume of the tumor region, histogram of the intensities in the tumor region, etc. To determine these features, the facility first identifies/segments out the tumor and pancreatic regions either manually with expert's knowledge or employing automated techniques for pancreatic and tumor segmentation like convolutional network for semantic segmentation. For calculating image features like average intensity and histogram of intensities, the facility first uses the obtained segmentation map to mask the pancreatic or tumor regions. Then, from the masked-out region the facility calculates the intensities and the histogram of those regions. For calculating the volume of the tumor and pancreatic regions, the facility performs summation over the segmentation maps. In various embodiments, the facility also utilizes other image features such as SIFT (Scale Invariant Feature Transform) and SURF (Speeded-Up Robust Features) image features. Both of these can be used as image features or descriptors. The goal of a descriptor is to provide a unique and robust description of an image feature, e.g., by describing the intensity distribution of the pixels within the neighborhood of the point of interest. Most descriptors are computed by the facility in a local manner, hence a description is obtained for every point of interest. Features can also be extracted from a deep learning based classifier. Features for an image can be extracted using a deep network. To do this, in some embodiments the facility uses a deep network pretrained on a large dataset with millions of images called ImageNet. The facility obtains the image features by performing a forward pass on a pre-trained deep network, such as a network obtained from a deep learning environment such as Google Tensor-Flow. The facility uses the vectors obtained from the second last fully connected layer as feature for the image.

In act 203, the facility accesses one or more electronic health records containing patient clinical data. In act 204, the facility extracts features from this accessed clinical data.

In act 205, the facility combines the features extracted from the scans and the clinical text to obtain a single feature vector for a particular patient. For combining the features, the facility concatenates or merges the feature vectors of scans and the clinical data. In act 206, the facility performs preprocessing and imputation for missing data. In some embodiments, the facility employs an imputation technique called MICE—Multivariate Imputation by Chained Equations (MICE)—which has emerged as a useful technique for imputing missing data. MICE operates under the assumption that missing data are missing at random. Also in act 206, the facility splits the data into a training dataset 207 and a validation dataset 208. In act 209, the facility uses the training data set to train a statistical model—such as a random forest survival regression classification model—to predict the dependent variables and global risk score (which represents the probability that overall survival time will exceed a specific duration—in some embodiments a number in arbitrary scale for which a higher value indicates higher risk).

After the model is trained in act 209, in act 210, the facility uses the testing dataset 208 to test the trained model, and identify any changes needed to reach an adequate level of prediction efficacy.

After training and testing, in act 210, the facility uses the model to predict global risk score and overall survival time for particular patients. Thus, the framework serves as an important tool in the cancer analysis and aid the clinicians and the trialists to take appropriate actions with the help of model predictions.

A random survival forest (RSF) is a non-parametric and a non-linear model used by the facility in some embodiments for survival analysis. It performs well compared with other survival analysis methods in terms of discrimination ability, ability to identify non-linear effects, and ability to identify important predictors that can discriminate survival function. Random survival forest (RSF) is an extension of random forest for survival analysis that handles difficulties, such as high variance, incapability in modeling non-linear effects of multiple variable, etc., that are encountered in traditional models such as Cox proportional hazards models. RSF automatically assesses the complex effects and interactions among all variables from objective view, following the inherent relationship between any factors and the predictive result, Random Forest (RF) is a model containing a large number of decision trees that:

a) are based on bootstrap samples; tree is based on a random sample with replacement of all observations.

b) where each tree division is based on a random sample of predictors.

c) There is no pruning; trees are as long as possible.

For building each RF tree in the forest, a different portion of the observations is not used in training the tree, but is reserved for post-training evaluation of the tree (approximately 37%, in some embodiments). This is called out-of-bag (OOB) sample and is used for a honest estimate of the model predictive capability. Random Survival Forest (RSF) is a class of survival prediction models, those that use data on the life history of subjects (the response) and their characteristics (the predictor variables). In this case, it extends the RF algorithm for a target which is not a class, or a number, but a survival curve. There are four families of random forests: regression forests for continuous responses classification forests for factor responses Survival forests for right-censored survival settings competing risk survival forests for competing risk scenarios. RF can effectively analyze a large number of variables, of many different types, with no previous variable selection process. RSF is generally not parametric, and in particular for survival target it does not assume the proportional risks assumption.

Figure 3:
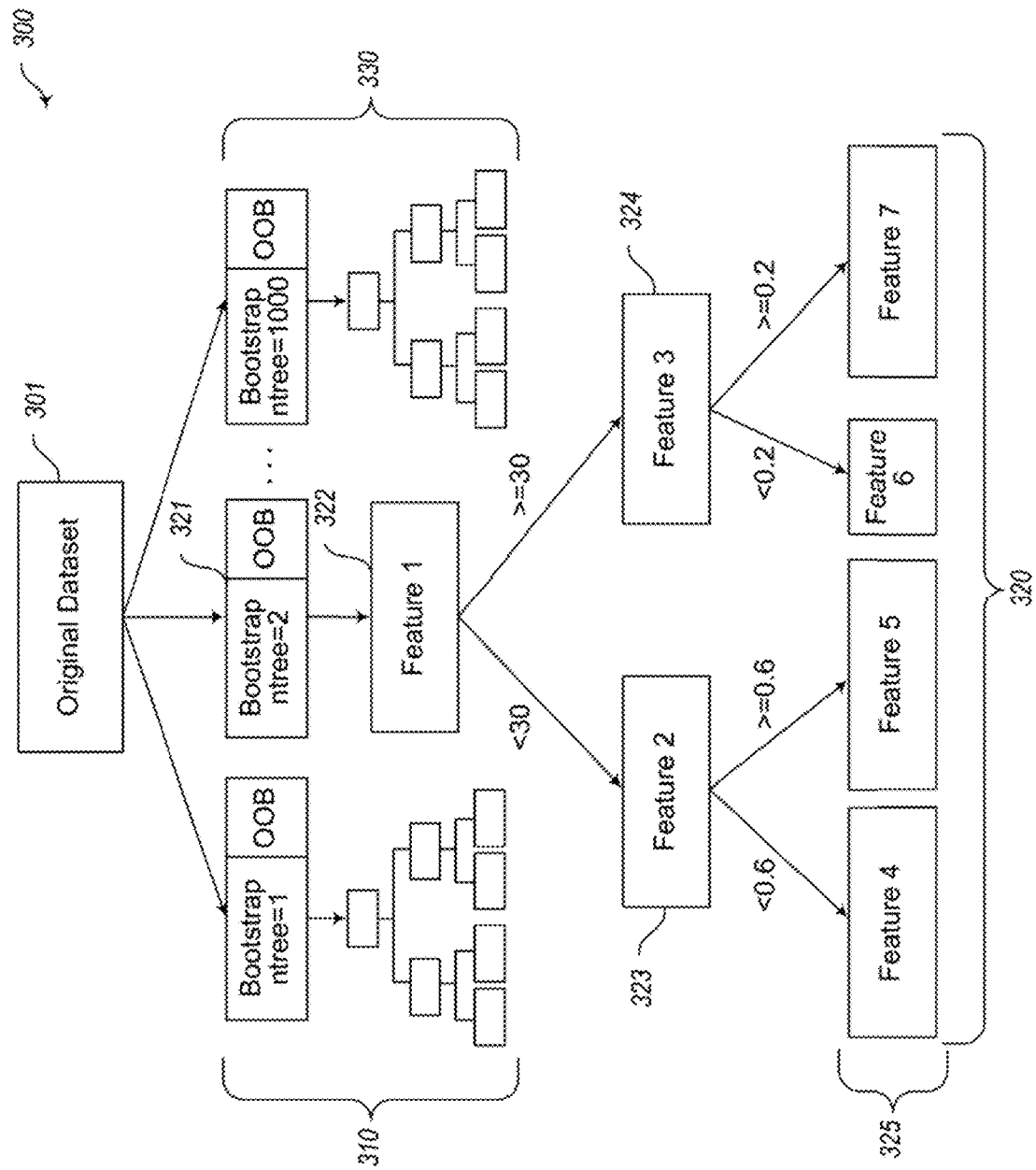
FIG. 3 is a model diagram showing a sample random survival forest model constructed and trained by the facility in some embodiments.

FIG. 3 is a model diagram showing a sample random survival forest model constructed and trained by the facility in some embodiments. This mode is based on original data set 301, and is made up of a number of decision trees, including shown trees 310, 320, and 330. Each tree has a header node that identifies the tree, such as header node 321 for tree 320, as well as the out-of-bag observations reserved by the facility for evaluating the tree. Each tree has a root node, such as root note 322 in tree 320, that identifies a feature used in the tree to classify a patient. The edges connecting root note 322 to its children 323 and 324 each specify a range of this first feature that maps a patient to one of the two child nodes. For example, for child node 323, the edge from root node 322 specifies that a range of "<30" of feature 1 maps the patient to child node 323, while the edge from root node 322 to child node 324 specifies that a range of ">=30" maps the patient to child node 324. For example, the facility would map a patient having the value of 32 for feature 1 to child node 324. Subsequent levels of the tree, such as level 325, each perform further classification based upon different ranges of the same or other features.

Ultimately, each leaf of each tree corresponds to a different prediction of a dependent variable. To evaluate the forest to make a prediction for a particular patient, the facility traverses each of the trees based upon the patient's feature values, following the edges or branches specifying feature ranges containing the patient's feature values, from each tree's node to a leaf of the tree. The facility then aggregates the dependent variable values specified by the leaf reached in each tree, in order to obtain a dependent variable value prediction for the patient for the entire forest. In various embodiments, the facility uses aggregation fractions for this purpose, such as median, mean, mode, sum, product, etc.

In various embodiments, the facility provides a variety of visual user interfaces that assist clinicians and others to obtain information about clinical trials and predictions made from them by the facility.

Figure 4:
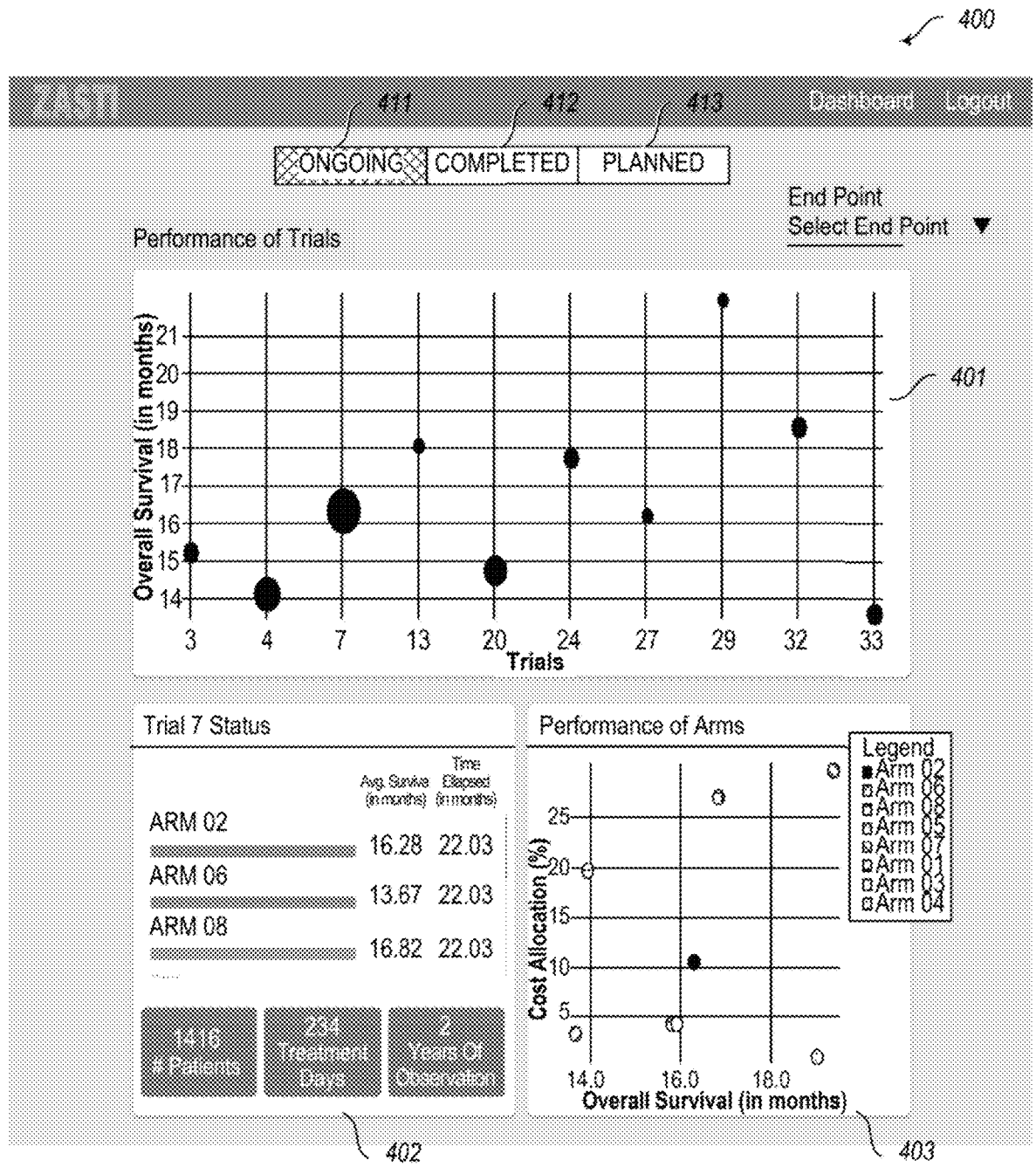
FIG. 4 is a display diagram showing a customizable clinical trials dashboard presented by the facility in some embodiments.

FIG. 4 is a display diagram showing a customizable clinical trials dashboard presented by the facility in some embodiments. The dashboard 400 contains charts 401, 402 and 403 each showing information about an overall survival rate metric. In various embodiments, the facility presents similar dashboards for a variety of other outcome metrics, including progression-free survival, adverse reaction, and others. The dashboard also includes controls for 411-413 that the user can select in order to show information in the displayed charts relating to ongoing trials, completed trials and planned trials, respectively.

Figure 5:
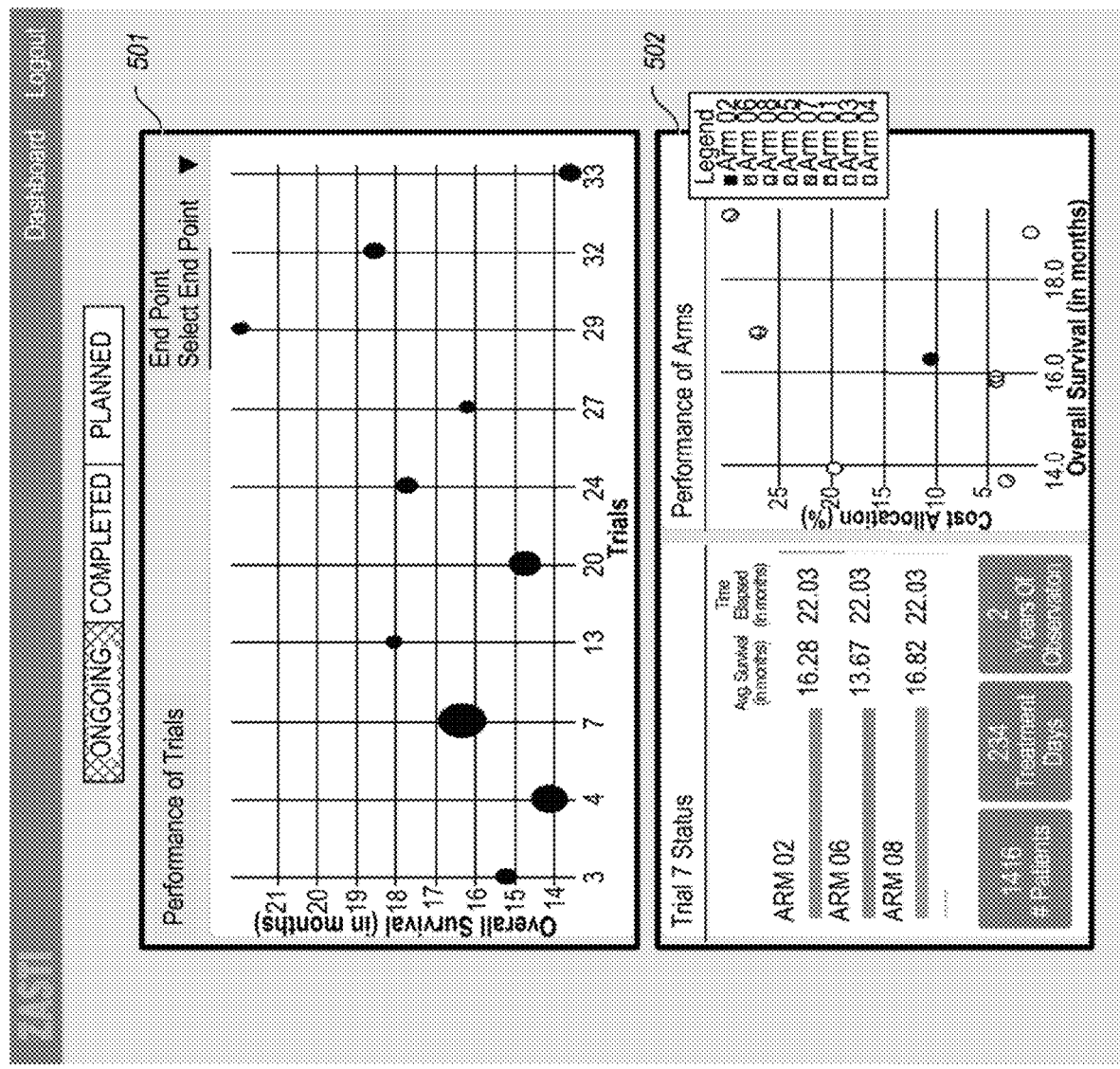
FIG. 5 is a display diagram showing a sample ongoing trials details user interface presented by the facility in some embodiments.

FIG. 5 is a display diagram showing a sample ongoing trials details user interface presented by the facility in some embodiments. The user interface 500 includes charts 501 and 502. In chart 501, the results of trials are measured in terms of overall survival rate. Size of each bubble indicates a cost allocation for that trial estimated using industry averages for each trial and phase in oncology. If the cost allocation to a trial is high and survival of a particular trial is less than average survival for all trials, then this trial may not be cost efficient. A manager can look at this and propose reallocation of the associated cost resources or just drop the trial or ARM. In chart 502, on selecting a trial, status and performance of various ARMs within the trial can be monitored here. The facility assess the performance of different ARMs as follows: red, for survival is estimated of a particular ARM<Average survival of trial, while for green, survival of a particular ARM>Average survival of trial.

Figure 6:
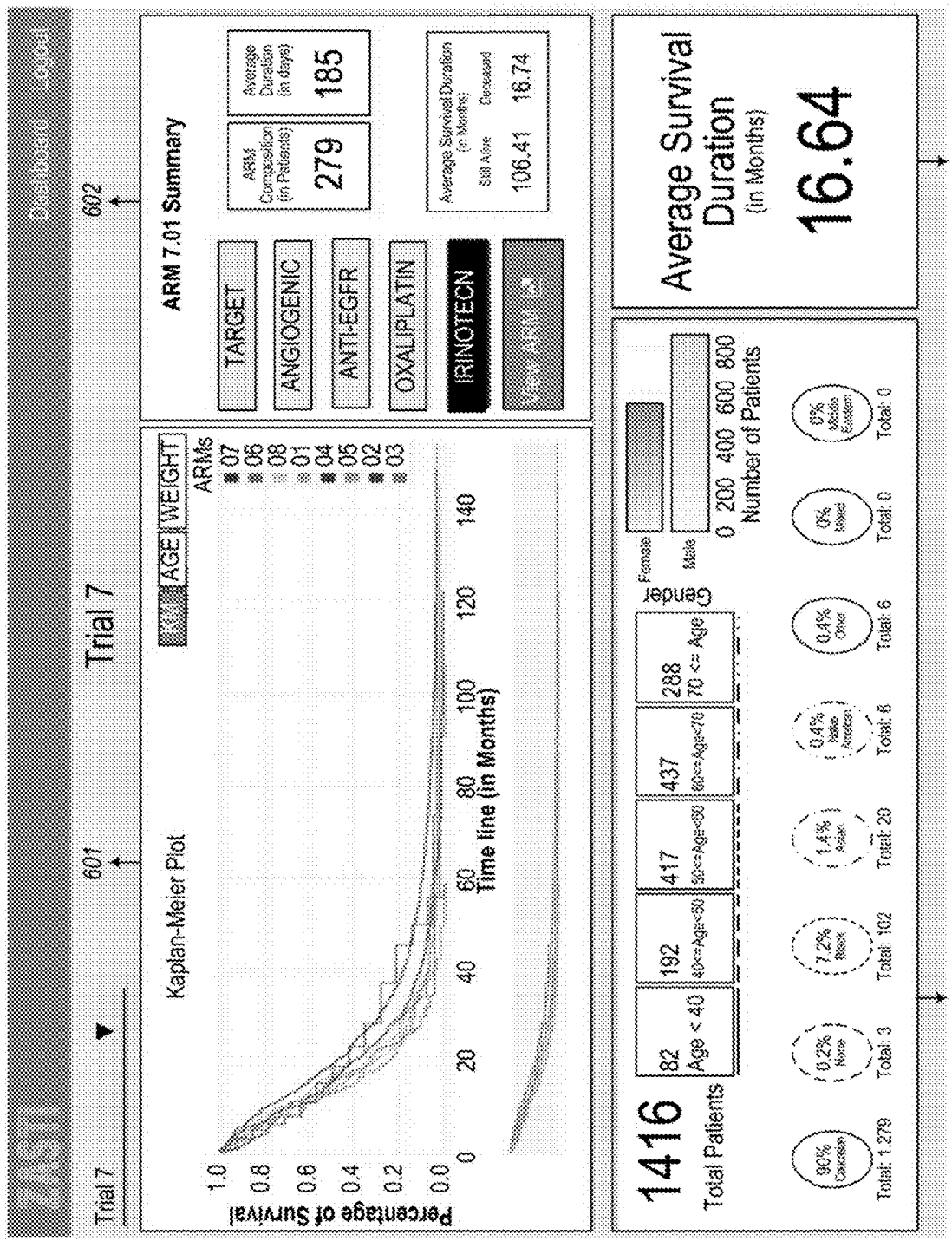
FIG. 6 is a display diagram showing a sample trial dashboard user interface presented by the facility in some embodiments.

FIG. 6 is a display diagram showing a sample trial dashboard user interface presented by the facility in some embodiments. 600 is made up of charts 601-604. Chart 601 contains Kaplan-Meier survival curves, which graphically display the time until study participants developed a particular event or endpoint, often death, or an event such as recurrence of cancer. A trial contains different ARMs corresponding to different treatments. Percentage survival for different ARMs is displayed. Chart 602 summarizes this trial's 5 treatment regimens and ARMs corresponding to combinations of these regimens is displayed. It also provides a summary of a particular ARM in the current trial and facility to drill down into further analysis of an ARM. Chart 603 shows demographics aggregates (age, gender and ethnicity distribution) for the trial. Chart 604 shows Average Survival Duration—the average survival time for the deceased and alive patients separately in this trial.

Figure 7:
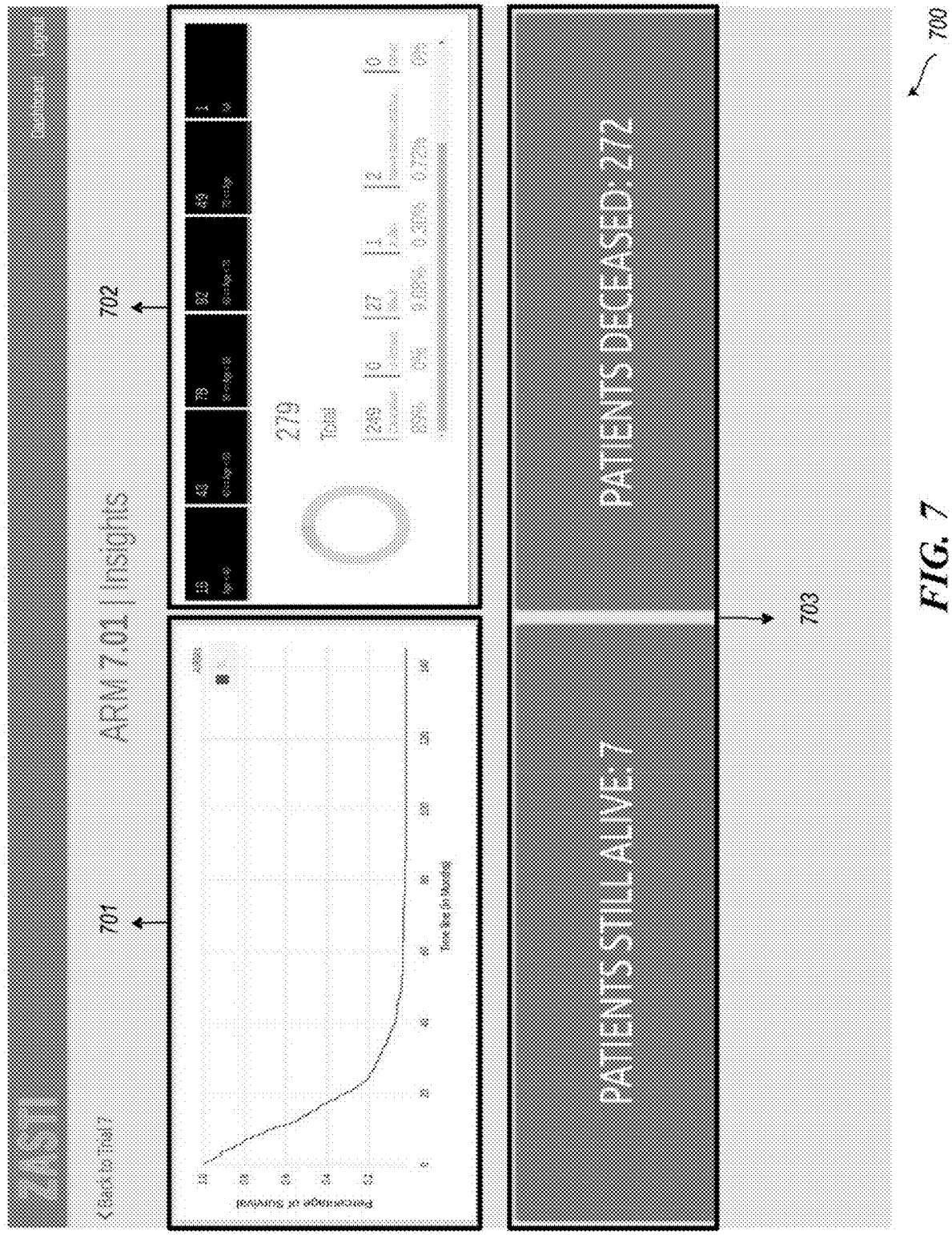
FIG. 7 is a display diagram showing a sample ARM dashboard user interface presented by the facility in some embodiments.

FIG. 7 is a display diagram showing a sample ARM dashboard user interface presented by the facility in some embodiments. The user interface 700 includes charts 701, 702, and 703, together portraying the responsiveness of patients in the ARM to treatment in accordance with the ARM. Chart 701 contains a Kaplan curve showing the progression of the ARM in terms of survival percentage versus time. Chart 702 shows demographics for the ARM, such as age, gender, and ethnicity distributions. Chart 703 shows alive and deceased patient aggregates for the ARM. The values change as the user moves forward in the ARM by hovering on the curve. Individual patient progress can be monitored.

Figure 8:
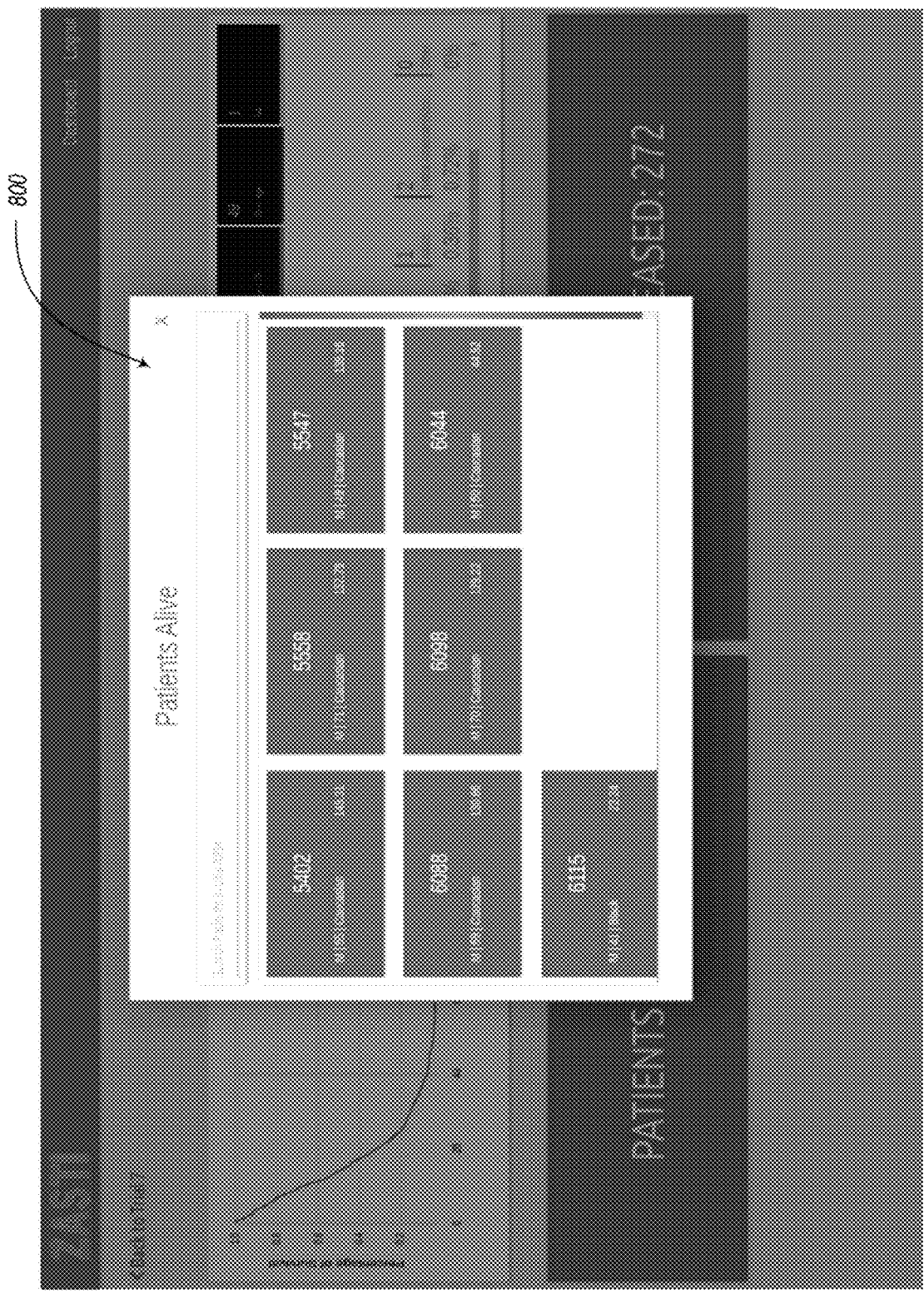
FIG. 8 is a display diagram showing a sample snapshot interface presented by the facility in some embodiments.

FIG. 8 is a display diagram showing a sample snapshot interface presented by the facility in some embodiments. The user interface 800 shows an overview of the Patients Alive or Deceased along the duration of the trial. As time passes, the number of patients who are dead changes, enabling performance of the drug can be monitored. In this case, the provided overview is of patients who are alive, selected based on the user clicking on the patients still alive aggregate shown in FIG. 7. The user can cause a similar overview to be displayed for patients deceased by clicking on this aggregate in FIG. 7. An individual patient progress report can be examined either by directly clicking on the patient card or searching for the patient id on the search bar.

Figure 9:
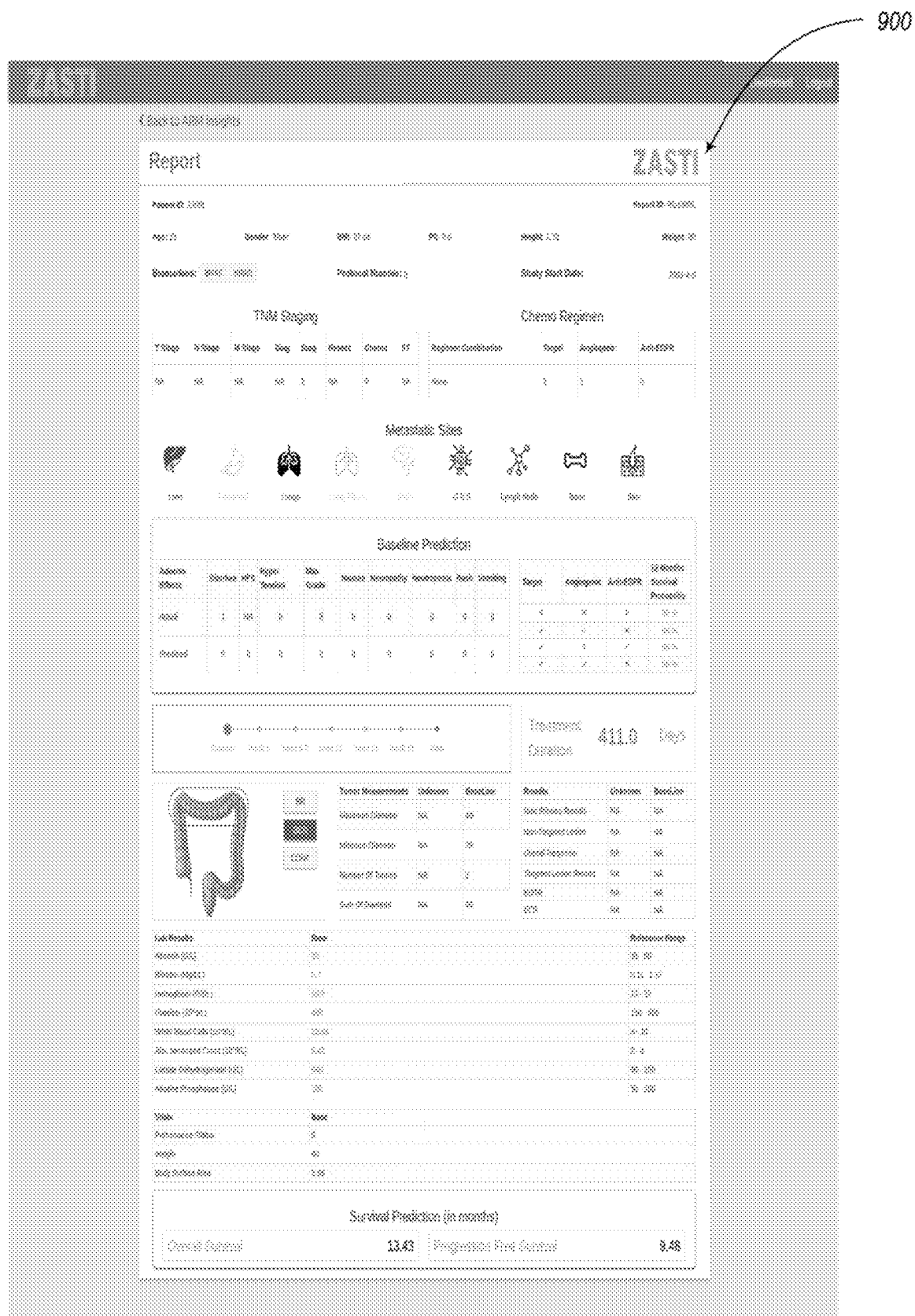
Figure 10:
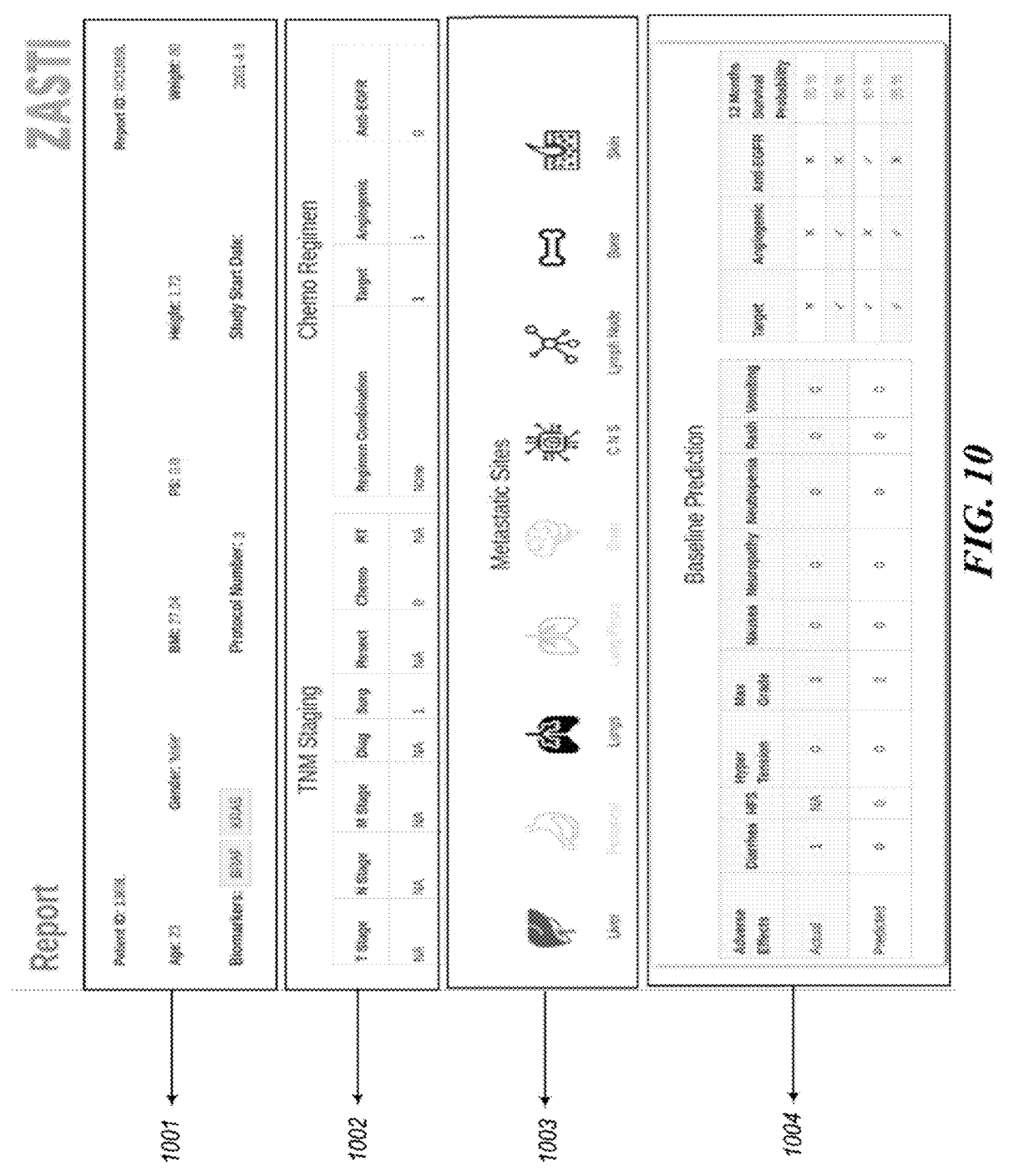
Figure 11:
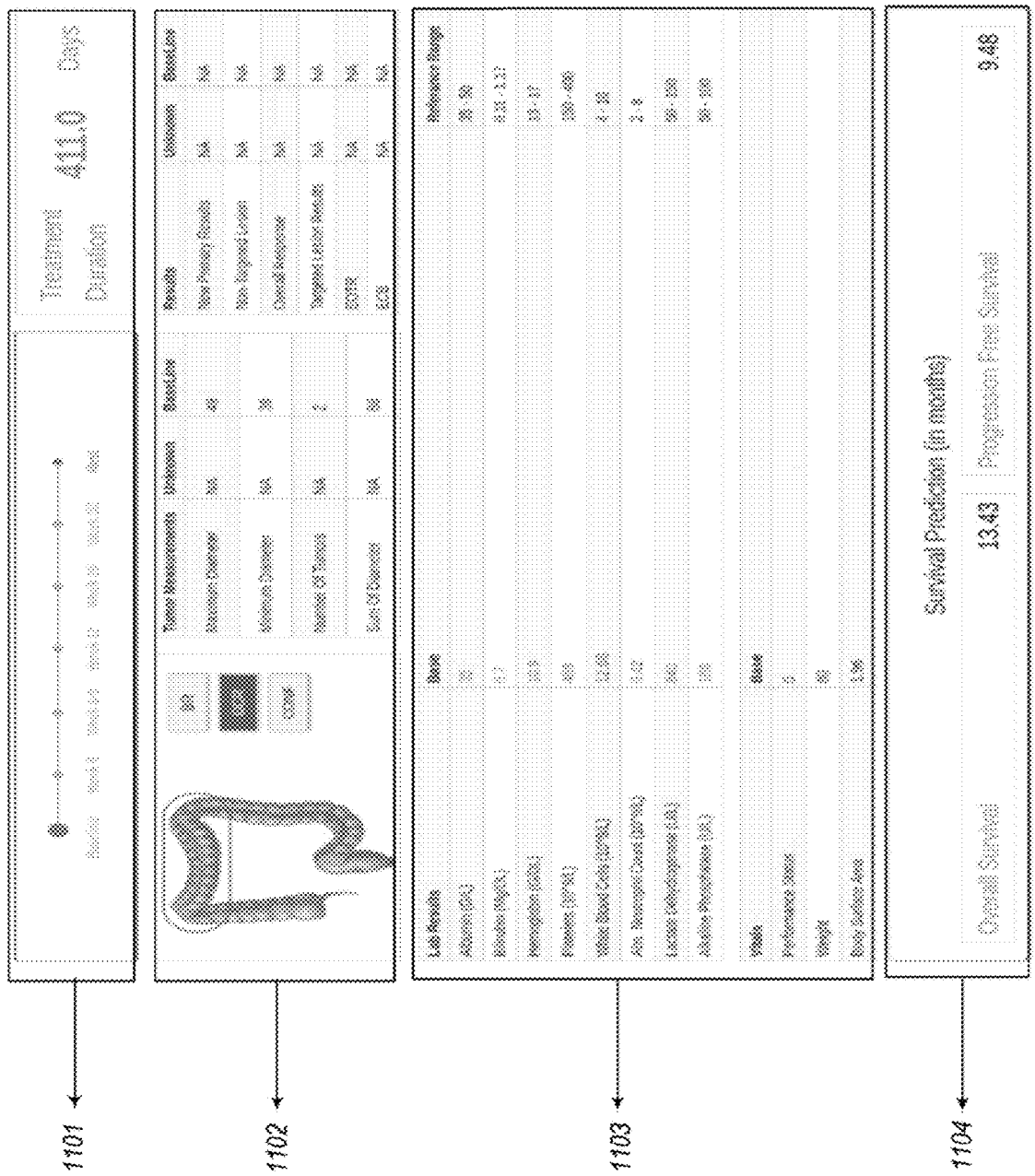

FIGS. 9-11 are display diagrams showing a sample patient test results report presented by the facility in some embodiments. The report 900 contains various information about the patient's test results.

FIGS. 10 and 11 show the top and bottom halves of the patient test results report from FIG. 9 in greater detail. Referring to FIG. 10, in section 1001, the report contains clinical data values for the patient—including prior treatments and tests undertaken—without identifying information. Section 1002 of the report contains a TMM classification of the patient's malignant tumors, and the patient's chemotherapy regimen or regimens. TNM Classification of Malignant Tumors is a globally recognized standard for classifying the extent of spread of cancer. A chemotherapy regimen is a regimen for chemotherapy, defining the drugs to be used, their dosage, the frequency and duration of treatments, and other considerations. Section 1003 of the report identifies the patient's Metastatic Sites: Red indicates-Site has been affected, Black-Tests have been taken, Grey-No tests taken. Section 1004 of the report contains a baseline prediction for the patient. From baseline data or at the start of the trial, the facility predicts whether or not the patient will survive after 12 months if given different treatment regimens.

Referring to FIG. 11, in section 1101, the report shows the progression of the patient over different time intervals. Section 1102 shows the primary organ that has been affected; the location of the cancer in the organ and other details about the tumor are captured here. Section 1103 evaluates the progression of patient through an ARM, i.e., all the test and lab results are represented from week 0 to week 52. Values in red indicate below normal and green indicate normal. Section 1104 shows the overall survival rate predicted for the patient. The prediction is made in terms of overall survival and progression free survival as end points. The report indicates that this patient will survive after 12 months for any combination of treatment regimen, Our prediction: 13.43 months.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

We claim:

1. A method for forecasting a clinical outcome for a subject patient based on a clinical trial involving a group of patients, comprising:
    obtaining patient image data for patients of the group;
    extracting features from the obtained patient image data for patients of the group, wherein the features are extracted by using a scale invariant feature transform;
    obtaining patient electronic health record data for patients of the group;
    extracting features from the obtained electronic health record data for patients of the group;
    for each patient of the group, concatenating the extracted features;
    obtaining a value of the clinical outcome for patients of the group;
    using the extracted features concatenated for each member of the group, and clinical outcome values obtained for each member of the group, training a random survival forest regression model that forecasts the clinical outcome;
    obtaining patient image data for the subject patient;
    extracting features from the obtained patient image data for the subject patient;
    obtaining patient electronic health record data for the subject patient;
    extracting features from the obtained electronic health record data for the subject patient;
    concatenating the extracted features for the subject patient;
    applying the random forest regression model to the concatenated extracted features for the subject patient to obtain a prediction of the clinical outcome for the subject patient; and
    causing a treatment plan of the subject patient to be altered based, at least in part, on the prediction of the clinical outcome for the subject patient, the alteration being with respect to operation of a treatment device.

2. The method of claim 1 wherein the clinical outcome is overall survival time.

3. The method of claim 1 wherein the clinical outcome is global risk score.

4. The method of claim 1 wherein the subject patient is a human patient.

5. The method of claim 1 wherein the clinical outcome is a cancer survival outcome.

6. One or more storage devices collectively storing a medical outcome prediction model data structure, the data structure comprising:
    a trained statistical model that can be applied to image data and electronic health record data for a patient to predict a cancer survival outcome for the patient, wherein the trained statistical model is a random survival forest regression model, wherein missing image data and missing electronic health record data is imputed by using multivariate imputation by chained equations, wherein the cancer survival outcome is obtained by:
    obtaining patient image data for the patient;
    extracting features from the obtained patient image data for the subject patient;
    obtaining patient electronic health record data for the subject patient;
    extracting features from the obtained electronic health record data for the subject patient;
    concatenating the extracted features for the subject patient; and
    applying the random forest survival regression model to the concatenated extracted features for the subject patient; and
    user interface data adapted to present the cancer survival outcome for the patient and obtain user input as a basis for altering a treatment plan for the patient, the alteration being with respect to operation of a treatment device.

7. The storage devices of claim 6 wherein the model is a deep learning-based classifier.

8. The storage devices of claim 6 wherein the model is applied to patient image data via a tumor average intensity feature.

9. The storage devices of claim 6 wherein the model is applied to patient image data via a tumor intensity histogram feature.

10. The storage devices of claim 6 wherein the model is applied to patient image data via a tumor volume feature.

11. The storage devices of claim 6 wherein the model is applied to patient image data via a scale invariant feature transform feature.

12. The storage devices of claim 6 wherein the model is applied to patient image data via a speeded-up robust feature.

13. One or more hardware storage devices collectively having contents configured to cause a computing system to perform a method for predicting a clinical outcome for a subject patient based on a clinical trial involving a group of patients, the method comprising:
 obtaining patient image data for patients of the group;
 extracting features from the obtained patient image data for patients of the group, wherein the features are extracted by using speeded-up robust features;
 obtaining patient electronic health record data for patients of the group;
 extracting features from the obtained electronic health record data for patients of the group;
 for each patient of the group, concatenating the extracted features;
 obtaining a value of the clinical outcome for patients of the group;
 using the extracted features concatenated for each member of the group, and clinical outcome values obtained for each member of the group, training a statistical model to predict the clinical outcome;
 obtaining patient image data for the subject patient;
 extracting features from the obtained patient image data for the subject patient;
 obtaining patient electronic health record data for the subject patient;
 extracting features from the obtained electronic health record data for the subject patient;
 concatenating the extracted features for the subject patient;
 identifying one or more treatment options for the subject patient;
 applying the random survival forest regression model to the concatenated extracted features for the subject patient and the one or more treatment options for the subject patient to obtain a prediction of the clinical outcome for each of the treatment options for the subject patient; and
 causing the prediction of the clinical outcome for each of the treatment options for the subject patient to be presented to a user of the computing system; and
 in response to user input, causing a treatment plan of the subject patient to be altered based, at least in part, on the user input and the prediction of the clinical outcome for each of the treatment options for the subject patient, the alteration being with respect to operation of a treatment device.

14. The one or more hardware storage devices of claim 13 wherein the extracting features from the obtained patient image data for each patient comprises:
 in each of one or more images from the patient, segmenting a tumor region and/or a pancreatic region; and
 performing visual analysis of the segmented region or regions to obtain a feature value.

15. The one or more hardware storage devices of claim 13, the method further comprising:
 for a distinguished patient, among patient image data for the patient and patient electronic health record data for the patient, identifying missing data;
 determining imputed data for the patient corresponding to the identified missing data; and
 adding the determined imputed data to the data for the distinguished patient to obtain enhanced data for the distinguished patient, and
 wherein features are extracted from the obtained enhanced data for the distinguished patient.

16. The one or more hardware storage devices of claim 13 wherein multivariate imputation by chained equations is used to determine the imputed data.

17. The one or more hardware storage devices of claim 13 wherein the trained statistical model is a random forest survival regression model.

18. The one or more hardware storage devices of claim 13 wherein the trained statistical model is a deep learning-based classifier.

* * * * *